United States Patent
Ferrandez-Escamez et al.

(10) Patent No.: US 11,133,091 B2
(45) Date of Patent: Sep. 28, 2021

(54) AUTOMATED ANALYSIS SYSTEM AND METHOD

(71) Applicant: Nuance Communications, Inc., Burlington, MA (US)

(72) Inventors: Oscar Ferrandez-Escamez, Melrose, MA (US); John E. Ortega, Jr., New York, NY (US); Neil Barrett, Longueuil (CA); Brian Delaney, Bolton, MA (US); Ravi Kumar Kondadadi, Lakeville, MN (US)

(73) Assignee: Nuance Communications, Inc., Burlington, MA (US)

( * ) Notice: Subject to any disclaimer, the term of this patent is extended or adjusted under 35 U.S.C. 154(b) by 209 days.

(21) Appl. No.: 16/026,641

(22) Filed: Jul. 3, 2018

(65) Prior Publication Data
US 2019/0027235 A1    Jan. 24, 2019

Related U.S. Application Data

(60) Provisional application No. 62/535,522, filed on Jul. 21, 2017.

(51) Int. Cl.
*G16H 10/60* (2018.01)
*G06Q 30/04* (2012.01)
(Continued)

(52) U.S. Cl.
CPC .............. *G16H 10/60* (2018.01); *G06Q 20/14* (2013.01); *G06Q 30/04* (2013.01); *G16H 15/00* (2018.01); *G16H 40/20* (2018.01); *G16H 50/30* (2018.01)

(58) Field of Classification Search
CPC ........ G16H 40/20; G16H 15/00; G16H 50/30; G16H 10/60; G06Q 30/04; G06Q 20/14
See application file for complete search history.

(56) References Cited

U.S. PATENT DOCUMENTS

| | | | |
|---|---|---|---|
| 4,696,039 | A | 9/1987 | Doddington |
| 5,031,113 | A | 7/1991 | Hollerbauer |

(Continued)

FOREIGN PATENT DOCUMENTS

| | | |
|---|---|---|
| DE | 19533541 | 3/1997 |
| DE | 102007021284 | 11/2008 |

(Continued)

OTHER PUBLICATIONS

U.S. Appl. No. 14/924,214, filed Jun. 4, 2014, Spitznagel et al.
(Continued)

*Primary Examiner* — Eliza A Lam
(74) *Attorney, Agent, or Firm* — Wolf, Greenfield & Sacks, P.C.

(57) ABSTRACT

A method, computer program product, and computing system for processing content concerning a plurality of patients using a CAC system to define one or more billing codes concerning a social habit status of one or more patients of the plurality of patients. The one or more billing codes concerning the social habit status of the one or more patients are provided to a user for review. Feedback is received from the user concerning the accuracy of the one or more billing codes. The feedback concerning the one or more billing codes is automatically processed to define one or more confidence scores. The CAC system is trained based, at least in part, upon the one or more confidence scores.

20 Claims, 3 Drawing Sheets

(51) Int. Cl.
  *G16H 40/20* (2018.01)
  *G16H 50/30* (2018.01)
  *G06Q 20/14* (2012.01)
  *G16H 15/00* (2018.01)

(56) References Cited

U.S. PATENT DOCUMENTS

| | | |
|---|---|---|
| 5,051,924 A | 9/1991 | Bergeron et al. |
| 5,307,262 A | 4/1994 | Ertel |
| 5,680,511 A | 10/1997 | Baker et al. |
| 5,758,322 A | 5/1998 | Rongley |
| 5,787,394 A | 7/1998 | Bahl et al. |
| 5,909,667 A | 6/1999 | Leontiades et al. |
| 5,924,074 A | 7/1999 | Evans |
| 5,999,896 A | 12/1999 | Richardson et al. |
| 6,003,002 A | 12/1999 | Netsch |
| 6,073,101 A | 6/2000 | Maes |
| 6,173,259 B1 | 1/2001 | Bijl et al. |
| 6,212,498 B1 | 4/2001 | Sherwood et al. |
| 6,292,771 B1 | 9/2001 | Haug et al. |
| 6,360,237 B1 | 3/2002 | Schulz et al. |
| 6,366,882 B1 | 4/2002 | Bijl et al. |
| 6,418,410 B1 | 7/2002 | Nassiff et al. |
| 6,434,547 B1 | 8/2002 | Mishelevich et al. |
| 6,463,413 B1 | 10/2002 | Applebaum et al. |
| 6,487,530 B1 | 11/2002 | Lin et al. |
| 6,519,561 B1 | 2/2003 | Farrell et al. |
| 6,567,778 B1 | 5/2003 | Chao Chang et al. |
| 6,813,603 B1 | 11/2004 | Groner et al. |
| 6,915,254 B1 * | 7/2005 | Heinze .............. G06Q 50/24 704/9 |
| 7,233,938 B2 | 6/2007 | Carus et al. |
| 7,383,172 B1 | 6/2008 | Jamieson |
| 7,493,253 B1 | 2/2009 | Ceusters et al. |
| 7,610,192 B1 | 10/2009 | Jamieson |
| 7,983,922 B2 | 7/2011 | Neusinger et al. |
| 8,204,756 B2 | 6/2012 | Kim et al. |
| 8,208,641 B2 | 6/2012 | Oh et al. |
| 8,326,653 B2 | 12/2012 | Gottlieb et al. |
| 8,612,261 B1 * | 12/2013 | Swanson .......... G06F 19/3418 705/3 |
| 8,694,335 B2 | 4/2014 | Yegnanarayanan |
| 8,756,079 B2 | 6/2014 | Yegnanarayanan |
| 8,943,437 B2 | 1/2015 | Meurs |
| 9,324,321 B2 | 4/2016 | Xue et al. |
| 9,478,218 B2 | 10/2016 | Shu |
| 9,715,576 B2 | 7/2017 | Hayter, II |
| 9,892,734 B2 | 2/2018 | Koll et al. |
| 10,319,004 B2 | 6/2019 | Reiser et al. |
| 10,331,763 B2 | 6/2019 | Subramanian et al. |
| 10,366,424 B2 | 7/2019 | Spitznagel et al. |
| 10,366,687 B2 | 7/2019 | Zhan et al. |
| 10,373,711 B2 | 8/2019 | D'Souza et al. |
| 10,754,925 B2 | 8/2020 | D'Souza et al. |
| 10,902,845 B2 | 1/2021 | Zhan et al. |
| 10,949,602 B2 | 3/2021 | Snider et al. |
| 2003/0115083 A1 | 6/2003 | Masarie, Jr. et al. |
| 2003/0163461 A1 | 8/2003 | Gudbjartsson et al. |
| 2003/0212544 A1 | 11/2003 | Acero et al. |
| 2004/0044952 A1 | 3/2004 | Jiang et al. |
| 2004/0073458 A1 | 4/2004 | Jensen |
| 2004/0220831 A1 | 11/2004 | Fabricant |
| 2004/0220895 A1 | 11/2004 | Carus et al. |
| 2005/0033574 A1 | 2/2005 | Kim et al. |
| 2005/0228815 A1 | 10/2005 | Carus et al. |
| 2005/0240439 A1 | 10/2005 | Covit et al. |
| 2006/0136197 A1 | 6/2006 | Oon |
| 2006/0190300 A1 | 8/2006 | Drucker |
| 2006/0242190 A1 | 10/2006 | Wnek |
| 2007/0033026 A1 | 2/2007 | Bartosik et al. |
| 2007/0050187 A1 | 3/2007 | Cox |
| 2007/0088564 A1 | 4/2007 | March et al. |
| 2007/0208567 A1 | 9/2007 | Amento et al. |
| 2008/0002842 A1 | 1/2008 | Neusinger et al. |
| 2008/0004505 A1 | 1/2008 | Kapit et al. |
| 2008/0147436 A1 | 6/2008 | Ohlsson |
| 2008/0222734 A1 | 9/2008 | Redlich et al. |
| 2008/0255835 A1 | 10/2008 | Ollason et al. |
| 2008/0262853 A1 | 10/2008 | Jung et al. |
| 2008/0270120 A1 | 10/2008 | Pestian et al. |
| 2009/0109239 A1 | 4/2009 | Jain |
| 2009/0157411 A1 | 6/2009 | Kim et al. |
| 2009/0210238 A1 | 8/2009 | V |
| 2009/0216528 A1 | 8/2009 | Gemello et al. |
| 2009/0281839 A1 | 11/2009 | Lynn et al. |
| 2009/0326958 A1 | 12/2009 | Kim et al. |
| 2010/0023319 A1 | 1/2010 | Bikel et al. |
| 2010/0049756 A1 | 2/2010 | Chemitiganti et al. |
| 2010/0076772 A1 | 3/2010 | Kim et al. |
| 2010/0076774 A1 | 3/2010 | Breebaart |
| 2010/0161316 A1 | 6/2010 | Haug |
| 2010/0198602 A1 | 8/2010 | Oh et al. |
| 2010/0198755 A1 * | 8/2010 | Soil .............. G06F 19/324 706/11 |
| 2010/0250236 A1 | 9/2010 | Jagannathan et al. |
| 2010/0274584 A1 | 10/2010 | Kim |
| 2011/0040576 A1 | 2/2011 | Madan et al. |
| 2012/0078763 A1 * | 3/2012 | Koll .............. G06Q 30/04 705/34 |
| 2012/0089629 A1 | 4/2012 | Koll et al. |
| 2012/0109641 A1 | 5/2012 | Boone et al. |
| 2012/0215559 A1 | 8/2012 | Flanagan et al. |
| 2012/0245961 A1 | 9/2012 | Yegnanarayanan |
| 2013/0035961 A1 | 2/2013 | Yegnanarayanan |
| 2013/0041685 A1 | 2/2013 | Yegnanarayanan |
| 2013/0067319 A1 | 3/2013 | Olszewski et al. |
| 2013/0073301 A1 | 3/2013 | Rao et al. |
| 2013/0080187 A1 | 3/2013 | Bacon et al. |
| 2013/0246098 A1 | 9/2013 | Habboush et al. |
| 2013/0297347 A1 | 11/2013 | Cardoza et al. |
| 2013/0297348 A1 | 11/2013 | Cardoza et al. |
| 2013/0318076 A1 | 11/2013 | Chiticariu et al. |
| 2014/0164023 A1 | 6/2014 | Yegnanarayanan |
| 2014/0244257 A1 | 8/2014 | Colibro et al. |
| 2014/0257803 A1 | 9/2014 | Yu et al. |
| 2014/0278460 A1 | 9/2014 | Dart et al. |
| 2014/0280353 A1 | 9/2014 | Delaney et al. |
| 2014/0343957 A1 | 11/2014 | Dejori |
| 2014/0372142 A1 | 12/2014 | Reddy |
| 2014/0372147 A1 | 12/2014 | White |
| 2014/0372216 A1 | 12/2014 | Nath et al. |
| 2015/0039299 A1 | 2/2015 | Weinstein et al. |
| 2015/0039301 A1 | 2/2015 | Senior et al. |
| 2015/0039344 A1 | 2/2015 | Kinney et al. |
| 2015/0046178 A1 | 2/2015 | Jindal |
| 2015/0066974 A1 | 3/2015 | Winn |
| 2015/0095016 A1 | 4/2015 | Karres et al. |
| 2015/0112680 A1 | 4/2015 | Lu |
| 2015/0134361 A1 | 5/2015 | Molenda |
| 2015/0142473 A1 * | 5/2015 | Sethumadhavan .... G16H 10/60 705/3 |
| 2015/0149165 A1 | 5/2015 | Saon |
| 2015/0161522 A1 | 6/2015 | Saon et al. |
| 2015/0161995 A1 | 6/2015 | Sainath et al. |
| 2015/0178874 A1 | 6/2015 | Harris et al. |
| 2015/0356057 A1 | 12/2015 | Subramanian et al. |
| 2015/0356198 A1 | 12/2015 | D'Souza et al. |
| 2015/0356246 A1 | 12/2015 | D'Souza et al. |
| 2015/0356260 A1 | 12/2015 | D'Souza et al. |
| 2015/0356458 A1 | 12/2015 | Berengueres et al. |
| 2015/0356646 A1 | 12/2015 | Spitznagel et al. |
| 2015/0356647 A1 | 12/2015 | Reiser et al. |
| 2015/0371634 A1 | 12/2015 | Kim |
| 2015/0379241 A1 | 12/2015 | Furst et al. |
| 2016/0012186 A1 | 1/2016 | Zasowski et al. |
| 2016/0085743 A1 | 3/2016 | Haley |
| 2016/0260428 A1 | 9/2016 | Matsuda et al. |
| 2016/0300034 A1 | 10/2016 | Huddar et al. |
| 2016/0364532 A1 | 12/2016 | Honeycutt et al. |
| 2017/0039326 A1 | 2/2017 | Stankiewicz et al. |
| 2017/0061085 A1 | 3/2017 | Nossal et al. |
| 2017/0104785 A1 | 4/2017 | Stolfo et al. |
| 2017/0116373 A1 | 4/2017 | Ginsburg et al. |
| 2017/0169815 A1 | 6/2017 | Zhan et al. |

(56) References Cited

U.S. PATENT DOCUMENTS

| | | |
|---|---|---|
| 2017/0300635 A1 | 10/2017 | Ganesan et al. |
| 2017/0323060 A1 | 11/2017 | D'Souza et al. |
| 2017/0323061 A1 | 11/2017 | D'Souza et al. |
| 2018/0032678 A1 | 2/2018 | Dandala et al. |
| 2018/0032679 A1 | 2/2018 | Dandala et al. |
| 2018/0052961 A1 | 2/2018 | Shrivastava et al. |
| 2018/0081859 A1 | 3/2018 | Snider et al. |
| 2018/0089373 A1 | 3/2018 | Matsuguchi et al. |
| 2018/0090142 A1 | 3/2018 | Li et al. |
| 2018/0119137 A1 | 5/2018 | Matsuguchi et al. |
| 2018/0373844 A1 | 12/2018 | Ferrandez-Escamez et al. |
| 2019/0080450 A1 | 3/2019 | Arar et al. |
| 2019/0130073 A1 | 5/2019 | Sun et al. |
| 2019/0325859 A1 | 10/2019 | Zhan et al. |
| 2019/0385202 A1 | 12/2019 | Reiser et al. |
| 2020/0126130 A1 | 4/2020 | Spitznagel et al. |
| 2020/0126643 A1 | 4/2020 | D'Souza et al. |

FOREIGN PATENT DOCUMENTS

| | | |
|---|---|---|
| EP | 1 361 522 | 11/2003 |
| WO | WO 98/19253 | 5/1998 |
| WO | WO 2013/133891 | 9/2013 |
| WO | WO 2015/084615 | 6/2015 |

OTHER PUBLICATIONS

U.S. Appl. No. 16/526,443, filed Jul. 30, 2019, Spitznagel et al.
U.S. Appl. No. 14/296,249, filed Jun. 4, 2014, Subramanian et al.
U.S. Appl. No. 16/402,867, filed May 3, 2019, Subramanian et al.
U.S. Appl. No. 14/296,256, filed Jun. 4, 2014, D'Souza et al.
U.S. Appl. No. 16/928,519, filed Jul. 14, 2020, D'Souza et al.
U.S. Appl. No. 14/296,274, filed Jun. 4, 2014, D'Souza et al.
U.S. Appl. No. 16/502,626, filed Jul. 3, 2019, D'Souza et al.
U.S. Appl. No. 14/296,295, filed Jun. 4, 2014, D'Souza et al.
U.S. Appl. No. 15/977,451, filed May 11, 2018, D'Souza et al.
U.S. Appl. No. 14/296,303, filed Jun. 4, 2014, Reiser et al.
U.S. Appl. No. 16/395,954, filed Apr. 26, 2019, Reiser et al.
U.S. Appl. No. 14/965,637, filed Dec. 10, 2015, Zhan et al.
U.S. Appl. No. 16/459,335, filed Jul. 1, 2019, Zhan et al.
U.S. Appl. No. 15/372,338, filed Dec. 7, 2016, D'Souza et al.
U.S. Appl. No. 15/336,905, filed Dec. 1, 2016, D'Souza et al.
U.S. Appl. No. 15/632,152, filed Jun. 23, 2017, Oscar et al.
U.S. Appl. No. 15/796,658, filed Oct. 27, 2017, Sun et al.
U.S. Appl. No. 15/710,319, filed Sep. 20, 2017, Snider et al.
International Search Report and Written Opinion for International Application No. PCT/US2015/033642 dated Sep. 9, 2015.
International Search Report and Written Opinion for International Application No. PCT/US2015/033130 dated Aug. 6, 2015.
International Search Report and Written Opinion for International Application No. PCT/US2015/033648 dated Aug. 11, 2015.
International Search Report and Written Opinion for International Application No. PCT/US2016/061326 dated Feb. 21, 2017.
International Preliminary Report on Patentability for International Application No. PCT/US2016/061326 dated Jun. 21, 2018.
International Search Report and Written Opinion for International Application No. PCT/US2017/052542 dated Dec. 14, 2017.
International Preliminary Report on Patentability for International Application No. PCT/US2017/052542 dated Apr. 4, 2019.
[No Author Listed], Asthma specificity and tobacco use highlight ICD-10-CM respiratory changes. HCPro. JustCoding News. 2014:4 pages.
[No Author Listed], Chronic lower respiratory diseases J40-J47. 2015 ICD-10-CM Diagnosis Codes. ICD10Data.com 2015:6 pages.
[No Author Listed], Injury, poisoning and certain other consequences of external causes S00-T88. 2015 ICD-10-CM Diagnosis Codes. ICD10Data.com. 2015:35 pages.
Abrash et al., Connectionist Speaker Normalization and Adaptation. Proc. EUROSPEECH'95. 1995:4 pages.
Aronow et al., Ad Hoc Classification of Radiology Reports. Journal of the American Medical Informatics Association. 1999;6(5):393-411.
Bateman et al., The Quest for the Last 5%: Interfaces for Correcting Real-Time Speech-Generated Subtitles. Interactive Posters. CHI 2000:2 pages.
Birnbaum et al., Report: A Voice Password System for Access Security. AT&T Technical Journal. 1986:7 pages.
Bisani et al., Automatic Editing in a Back-End Speech-to-Text System. Proceedings of ACL-08: HLT. 2008:114-20.
Cimiano et al., Learning concept hierarchies from text with a guided hierarchical clustering algorithm. In C. Biemann and G. Paas (eds.), Proceedings of the ICML 2005 Workshop on Learning and Extending Lexical Ontologies with Machine Learning Methods, Bonn, Germany. 2005:10 pages.
Fan et al., PRISMATIC: Inducing Knowledge from a Large Scale Lexicalized Relation Resource. Proceedings of the NAACL HLT 2010 First International Workshop on Formalisms and Methodology for Learning by Reading. Jun. 2010:122-127.
Ferrao et al., Clinical Coding Support Based on Structured Data Stored in Electronic Health Records. IEEE International Conference on Bioinformatics and Biomedicine Workshops. 2012:790-7.
Florian et al., A Statistical Model for Multilingual Entity Detection and Tracking. Proceedings of the Human Language Technologies Conference 2004 (HLT-NAACL'04). 2004:8 pages.
Gemello et al., Linear hidden transformations for adaptation of hybrid ANN/HMM Models. Speech Communication. 2007;49:827-35.
Gomez-Perez et al., An overview of methods and tools for ontology learning from texts. Knowledge Engineering Review. 2004;19(3):187-212.
Heng-Hsou et al., An Event-Driven and Ontology-Based Approach for the Delivery and Information Extraction of E-mails IEEE. 2000:103-9.
Hewitt et al., Real-Time Speech-Generated Subtitles: Problems and Solutions. ISCA Archive. 6th International Conference on Spoken Language Processing (ICSLP 2000). 2000:5 pages.
Mendonca et al., Extracting information on pneumonia in infants using natural language processing of radiology reports. Journal of Biomedical Informatics. 2005;38:314-21.
Naik, Speaker Verification: A Tutorial. IEEE Communications Magazine. 1990:42-8.
Newman et al., Speaker Verifcation Through Large Vocabulary Continuous Speech Recognition. Dragon Systems, Inc. 1996:4 pages.
Omar, Fast Approximate I-Vector Estimation Using PCA. IEEE Proc. ICASSP. 2015:4495-9.
Rosenberg, Evaluation of an Automatic Speaker-Verification System Over Telephone Lines. Manuscript received Sep. 9, 1975. The Bell System Technical Journal. 1976;55(6):723-44.
Salton et al., A Vector Space Model for Automatic Indexing. Communications of the ACM. Nov. 1975;18(11):613.
Saon et al., Speaker Adaptation of Neural Network Acoustic Models Using I-Vectors. IEEE. 2013:55-9.
Senior et al., Improving DNN speaker independence with I-vector inputs. 2014 IEEE International Conference on Acoustics, Speech and Signal Processing (ICASSP), IEEE. 2014:225-9.
Shvaiko et al., Ontology Matching OM-2008. Papers from the ISWC Workshop. 2008:271 pages.
Sistrom et al., Managing Predefined Templated and Macros for a Departmental Speech Recognition System Using Common Software. Journal of Digital Imaging. 2001;14(3):131-41.
Soderland et al., Automated Classification of Encounter Notes in a Computer Based Medical Record. MEDINFO 1995 Proceedings. 1995:9 pages.
Sonntag et al., A Discourse and Dialogue Infrastructure for Industrial Dissemination. German Research Center for AI (DFKI). Proceeding IWSDS'10 Proceedings of the Second international conference on Spoken dialogue systems for ambient environments. 2010:12 pages.
Sonntag et al., RadSpeech's Mobile Dialogue System for Radiologists. IUI'12. 2012:2 pages.

(56) References Cited

OTHER PUBLICATIONS

Suhm, Multimodal Interactive Error Recovery for Non-Conversation Speech User Interfaces. Dissertation. 1998:292 pages.

Taira et al., Automatic Structuring of Radiology Free-Text Reports. infoRAD. Radiology 2001;21:237-45.

Welty et al., Large Scale Relation Detection. Proceedings of the NAACL HLT 2010 First International Workshop on Formalisms and Methodology for Learning by Reading. Jun. 2010:24-33.

* cited by examiner

AUTOMATED ANALYSIS SYSTEM AND METHOD

RELATED APPLICATION(S)

This application claims the benefit of U.S. Provisional Application No. 62/535,522, filed on 21 Jul. 2017, the entire contents of which are incorporated herein by reference.

TECHNICAL FIELD

This disclosure relates to computer assisted coding systems and methods and, more particularly, to self-training computer assisted coding systems and methods.

BACKGROUND

As is known in the art, a computer assisted coding (CAC) system is a software platform that analyzes healthcare content and produces appropriate medical billing codes based upon specific phrases and/or terms that may be included within the healthcare content. As would be expected, such computer assisted coding system may be configured to process various types of healthcare content, examples of which may include but are not limited to text-based healthcare content and voice-based healthcare content.

Unfortunately, these computer assisted coding (CAC) systems may be less than accurate (e.g., may produce inaccurate billing codes) and, unfortunately, may require considerable time and human interaction to improve the accuracy of the same.

SUMMARY OF DISCLOSURE

In one implementation, a computer-implemented method is executed on a computing device and includes processing content concerning a plurality of patients using a CAC system to define one or more billing codes concerning a social habit status of one or more patients of the plurality of patients. The one or more billing codes concerning the social habit status of the one or more patients are provided to a user for review. Feedback is received from the user concerning the accuracy of the one or more billing codes. The feedback concerning the one or more billing codes is automatically processed to define one or more confidence scores. The CAC system is trained based, at least in part, upon the one or more confidence scores.

One or more of the following features may be included. The social habit status of one or more patients may include one or more of: a smoking status of one or more patients; a drinking status of one or more patients; and a drug use status of one or more patients. The content concerning a plurality of patients may include one or more of: voice-based content concerning the plurality of patients; and text-based content concerning the plurality of patients. Automatically processing the feedback concerning the one or more billing codes to define one or more confidence scores may include identifying a plurality of portions of the content that concern differing social habit statuses of one or more patients. Automatically processing the feedback concerning the one or more billing codes to define one or more confidence scores may further include defining a billing code accuracy score for each of the plurality of portions of the content that concern differing social habit statuses of one or more patients. Automatically processing the feedback concerning the one or more billing codes to define one or more confidence scores may further include defining the one or more confidence scores based, at least in part, upon the billing code accuracy score defined for each of the plurality of portions of the content that concern differing social habit statuses of one or more patients. Training the CAC system based, at least in part, upon the one or more confidence scores may include: defining a model based, at least in part, upon the one or more confidence scores; and applying the model to the output of the CAC system.

In another implementation, a computer program product resides on a computer readable medium and has a plurality of instructions stored on it. When executed by a processor, the instructions cause the processor to perform operations including processing content concerning a plurality of patients using a CAC system to define one or more billing codes concerning a social habit status of one or more patients of the plurality of patients. The one or more billing codes concerning the social habit status of the one or more patients are provided to a user for review. Feedback is received from the user concerning the accuracy of the one or more billing codes. The feedback concerning the one or more billing codes is automatically processed to define one or more confidence scores. The CAC system is trained based, at least in part, upon the one or more confidence scores.

One or more of the following features may be included. The social habit status of one or more patients may include one or more of: a smoking status of one or more patients; a drinking status of one or more patients; and a drug use status of one or more patients. The content concerning a plurality of patients may include one or more of: voice-based content concerning the plurality of patients; and text-based content concerning the plurality of patients. Automatically processing the feedback concerning the one or more billing codes to define one or more confidence scores may include identifying a plurality of portions of the content that concern differing social habit statuses of one or more patients. Automatically processing the feedback concerning the one or more billing codes to define one or more confidence scores may further include defining a billing code accuracy score for each of the plurality of portions of the content that concern differing social habit statuses of one or more patients. Automatically processing the feedback concerning the one or more billing codes to define one or more confidence scores may further include defining the one or more confidence scores based, at least in part, upon the billing code accuracy score defined for each of the plurality of portions of the content that concern differing social habit statuses of one or more patients. Training the CAC system based, at least in part, upon the one or more confidence scores may include: defining a model based, at least in part, upon the one or more confidence scores; and applying the model to the output of the CAC system.

In another implementation, a computing system includes a processor and memory is configured to perform operations including processing content concerning a plurality of patients using a CAC system to define one or more billing codes concerning a social habit status of one or more patients of the plurality of patients. The one or more billing codes concerning the social habit status of the one or more patients are provided to a user for review. Feedback is received from the user concerning the accuracy of the one or more billing codes. The feedback concerning the one or more billing codes is automatically processed to define one or more confidence scores. The CAC system is trained based, at least in part, upon the one or more confidence scores.

One or more of the following features may be included. The social habit status of one or more patients may include one or more of: a smoking status of one or more patients; a drinking status of one or more patients; and a drug use status of one or more patients. The content concerning a plurality of patients may include one or more of: voice-based content concerning the plurality of patients; and text-based content concerning the plurality of patients. Automatically processing the feedback concerning the one or more billing codes to define one or more confidence scores may include identifying a plurality of portions of the content that concern differing social habit statuses of one or more patients. Automatically processing the feedback concerning the one or more billing codes to define one or more confidence scores may further include defining a billing code accuracy score for each of the plurality of portions of the content that concern differing social habit statuses of one or more patients. Automatically processing the feedback concerning the one or more billing codes to define one or more confidence scores may further include defining the one or more confidence scores based, at least in part, upon the billing code accuracy score defined for each of the plurality of portions of the content that concern differing social habit statuses of one or more patients. Training the CAC system based, at least in part, upon the one or more confidence scores may include: defining a model based, at least in part, upon the one or more confidence scores; and applying the model to the output of the CAC system.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

Figure 1:
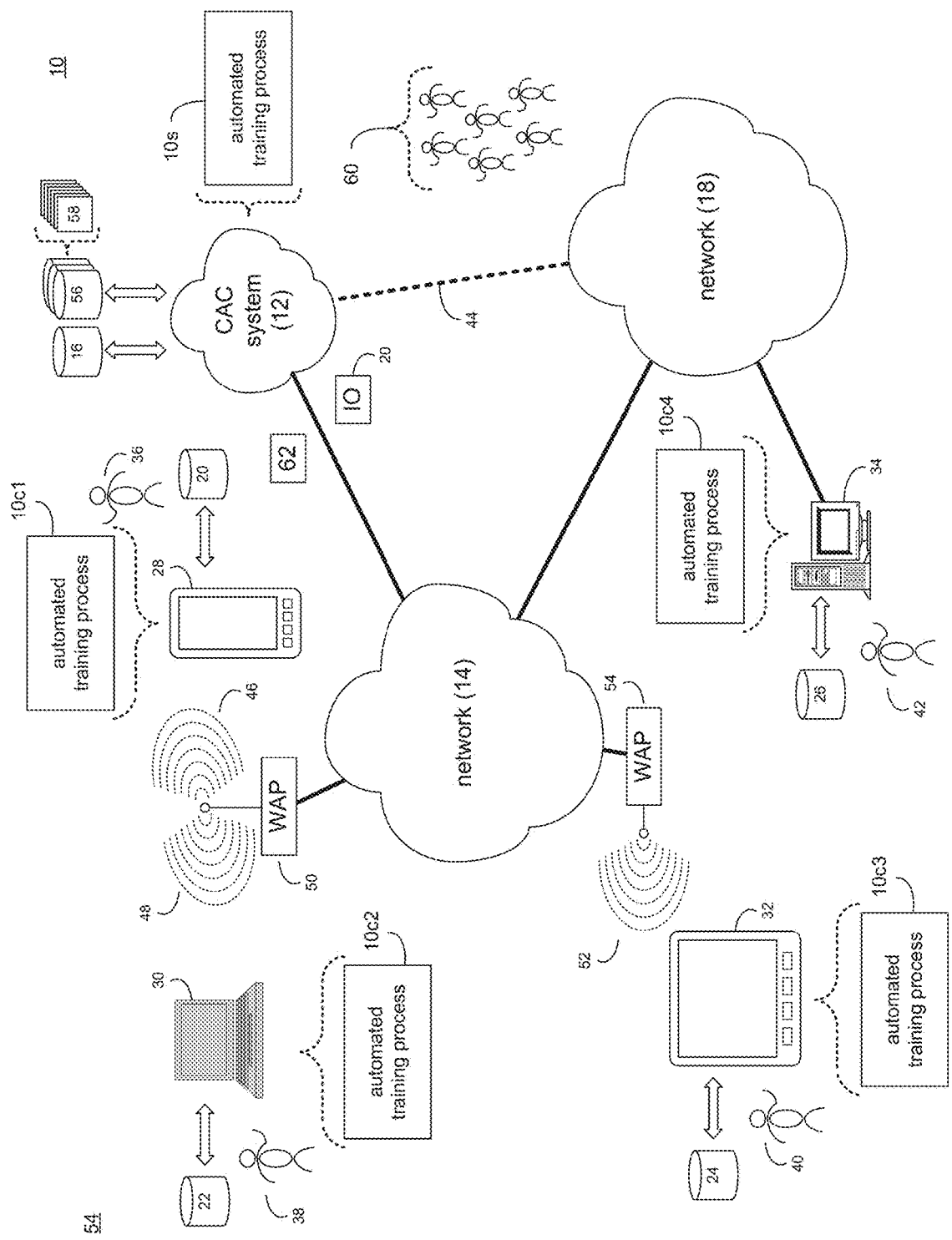
FIG. 1 is a diagrammatic view of a computer assisted coding system and an automated training process coupled to a distributed computing network.

System Overview:

Referring to FIG. 1, there is shown automated training process 10. As will be discussed below in greater detail, automated training process 10 may be configured to automate the training of computer assisted coding system 12.

Automated training process 10 may be implemented as a server-side process, a client-side process, or a hybrid server-side/client-side process. For example, automated training process 10 may be implemented as a purely server-side process via automated training process 10s. Alternatively, automated training process 10 may be implemented as a purely client-side process via one or more of automated training process 10c1, automated training process 10c2, automated training process 10c3, and automated training process 10c4. Alternatively still, automated training process 10 may be implemented as a hybrid server-side/client-side process via automated training process 10s in combination with one or more of automated training process 10c1, automated training process 10c2, automated training process 10c3, and automated training process 10c4.

Accordingly, automated training process 10 as used in this disclosure may include any combination of automated training process 10s, automated training process 10c1, automated training process 10c2, automated training process 10c3, and automated training process 10c4.

Automated training process 10s may be a server application and may reside on and may be executed by computer assisted coding system 12, which may be connected to network 14 (e.g., the Internet or a local area network). Computer assisted coding system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, one or more software applications, one or more software platforms, a cloud-based computational system, and a cloud-based storage platform.

As is known in the art, a SAN may include one or more of a personal computer, a server computer, a series of server computers, a mini computer, a mainframe computer, a RAID device and a NAS system. The various components of computer assisted coding system 12 may execute one or more operating systems, examples of which may include but are not limited to: Microsoft Windows Server™; Redhat Linux™, Unix, or a custom operating system, for example.

The instruction sets and subroutines of automated training process 10s, which may be stored on storage device 16 coupled to computer assisted coding system 12, may be executed by one or more processors (not shown) and one or more memory architectures (not shown) included within computer assisted coding system 12. Examples of storage device 16 may include but are not limited to: a hard disk drive; a RAID device; a random access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Various IO requests (e.g. IO request 20) may be sent from automated training process 10s, automated training process 10c1, automated training process 10c2, automated training process 10c3 and/or automated training process 10c4 to computer assisted coding system 12. Examples of IO request 20 may include but are not limited to data write requests (i.e. a request that content be written to computer assisted coding system 12) and data read requests (i.e. a request that content be read from computer assisted coding system 12).

The instruction sets and subroutines of automated training process 10c1, automated training process 10c2, automated training process 10c3 and/or automated training process 10c4, which may be stored on storage devices 20, 22, 24, 26 (respectively) coupled to client electronic devices 28, 30, 32, 34 (respectively), may be executed by one or more processors (not shown) and one or more memory architectures (not shown) incorporated into client electronic devices 28, 30, 32, 34 (respectively). Storage devices 20, 22, 24, 26 may include but are not limited to: hard disk drives; optical drives; RAID devices; random access memories (RAM); read-only memories (ROM), and all forms of flash memory storage devices.

Examples of client electronic devices 28, 30, 32, 34 may include, but are not limited to, data-enabled, cellular telephone 28, laptop computer 30, tablet computer 32, personal computer 34, a notebook computer (not shown), a server computer (not shown), a gaming console (not shown), a smart television (not shown), and a dedicated network device (not shown). Client electronic devices 28, 30, 32, 34 may each execute an operating system, examples of which may include but are not limited to Microsoft Windows™, Android™, WebOS™, iOS™, Redhat Linux™, or a custom operating system.

Users 36, 38, 40, 42 may access analysis process 10 directly through network 14 or through secondary network 18. Further, automated training process 10 may be connected to network 14 through secondary network 18, as illustrated with link line 44.

The various client electronic devices (e.g., client electronic devices 28, 30, 32, 34) may be directly or indirectly coupled to network 14 (or network 18). For example, data-enabled, cellular telephone 28 and laptop computer 30 are shown wirelessly coupled to network 14 via wireless communication channels 46, 48 (respectively) established between data-enabled, cellular telephone 28, laptop computer 30 (respectively) and cellular network/bridge 50, which is shown directly coupled to network 14. Further, personal tablet computer 32 is shown wirelessly coupled to network 14 via wireless communication channel 52 established between tablet computer 32 and wireless access point (i.e., WAP) 54, which is shown directly coupled to network 14. Additionally, personal computer 34 is shown directly coupled to network 18 via a hardwired network connection.

The Computer Assisted Coding System:

As will be discussed below in greater detail, computer assisted coding system 12 may be configured to access one or more datasources 56, examples of which may include but are not limited to one or more of a patient profile datasource, a medical records datasource, a medical notes datasource, an encounter records datasource, a voice recording datasource, and a billing code datasource.

Further, computer assisted coding system 12 may be configured to process content 58 (e.g., one or more medical records, one or more medical notes, one or more encounter records and/or one or more voice recording) included within datasource 56 so that one or more billing codes (e.g., defined within the billing code datasource) may be assigned to various patient encounters within a clinical environment with patients (e.g., defined within the patient profile datasource).

Examples of such a clinical environment may include but are not limited to: a doctor's office, a medical facility, a medical practice, a medical lab, an urgent care facility, a medical clinic, an emergency room, an operating room, a hospital, a long term care facility, a rehabilitation facility, a nursing home, and a hospice facility. Further, examples of such patient encounters may include but are not limited to a patient visiting one or more of the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility).

Figure 2:
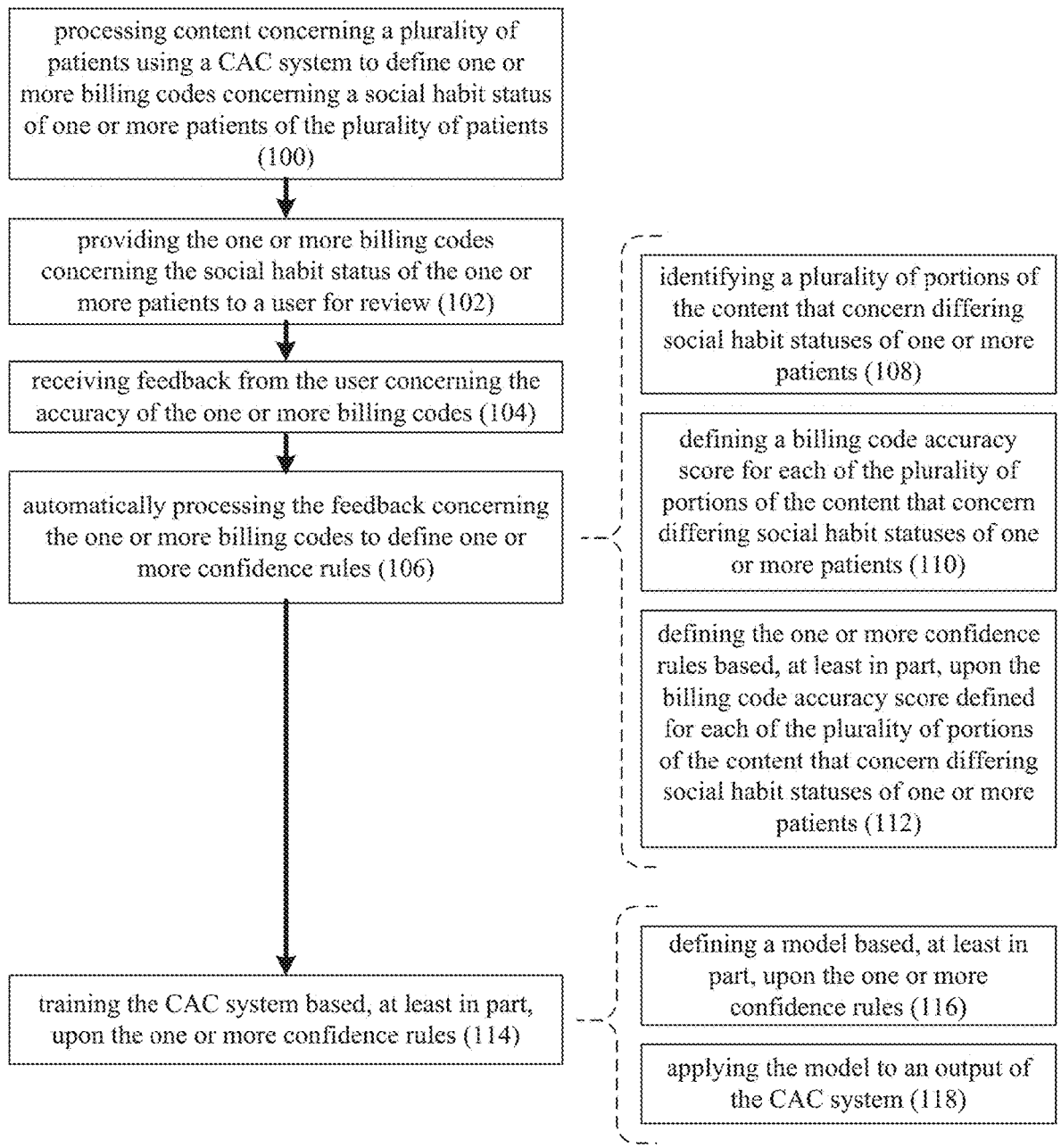
FIG. 2 is a flow chart of one implementation of the automated training process of FIG. 1.

The Automated Training Process:

Referring also to FIG. 2, automated training process 10 may process 100 content (e.g., content 58) concerning a plurality of patients (e.g., plurality of patients 60) using a CAC system (e.g., computer assisted coding system 12) to define one or more billing codes (e.g., billing codes 62) concerning a social habit status of one or more patients of the plurality of patients (e.g., plurality of patients 60).

Generally speaking, examples of content 58 concerning plurality of patients 60 may include but is not limited to one or more of: voice-based content concerning the plurality of patients (e.g., plurality of patients 60); and text-based content concerning the plurality of patients (e.g., plurality of patients 60). Further and generally speaking, the social habit status of the one or more patients may include one or more of: a smoking status of one or more of plurality of patients 60; a drinking status of one or more of plurality of patients 60; and a drug use status of one or more of plurality of patients 60.

For illustrative purposes, assume that content 58 includes one or more of medical records, medical notes, encounter records and/or voice recordings. For example, a portion of content 58 may be human-based or computer-based transcriptions of the above-stated voice recordings that results in text-based content. Further, a portion of content 58 may be hand-written notes by the medical professionals (e.g., doctors, nurses, physician's assistants, lab technicians, physical therapists and/or staff members involved in the patient encounter) that are processed to generate text-based content. Additionally, a portion of content 58 may be native text-based content (e.g., forms that are populated by medical professionals (e.g., doctors, nurses, physician's assistants, lab technicians, physical therapists and/or staff members involved in the patient encounter), patients (e.g., people that are visiting the above-described clinical environments for the patient encounter), and third parties (e.g., friends of the patient, relatives of the patient and/or acquaintances of the patient that are involved in the patient encounter).

For the following example, further assume that content 58 is one or more of medical records, medical notes, encounter records and/or voice recordings generated by a particular clinical environment (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility) during a defined period of time (e.g., a day, a week, or a month). Assume that at the end of this defined period, content 58 may be processed so that the appropriate insurance companies/providers may be billed.

As discussed above, computer assisted coding system 12 may be configured to process content 58 (e.g., one or more medical records, one or more medical notes, one or more encounter records and/or one or more voice recording) included within datasource 56 so that billing codes 62 (e.g., defined within the billing code datasource) may be assigned to various patient encounters (defined within content 58) and the appropriate insurance companies/providers may be billed.

Specifically, computer assisted coding system 12 may be configured to essentially mimic a human medical coder (not shown) who would have accessed/reviewed content 58 and manually assigned billing codes to the various patient encounters defined within content 58 so that the appropriate insurance companies/providers may be billed. And as computer assisted coding system 12 is a computerized process, the time spent by the medical coder (not shown) manually assigning billing codes may be drastically reduced.

Figure 3:
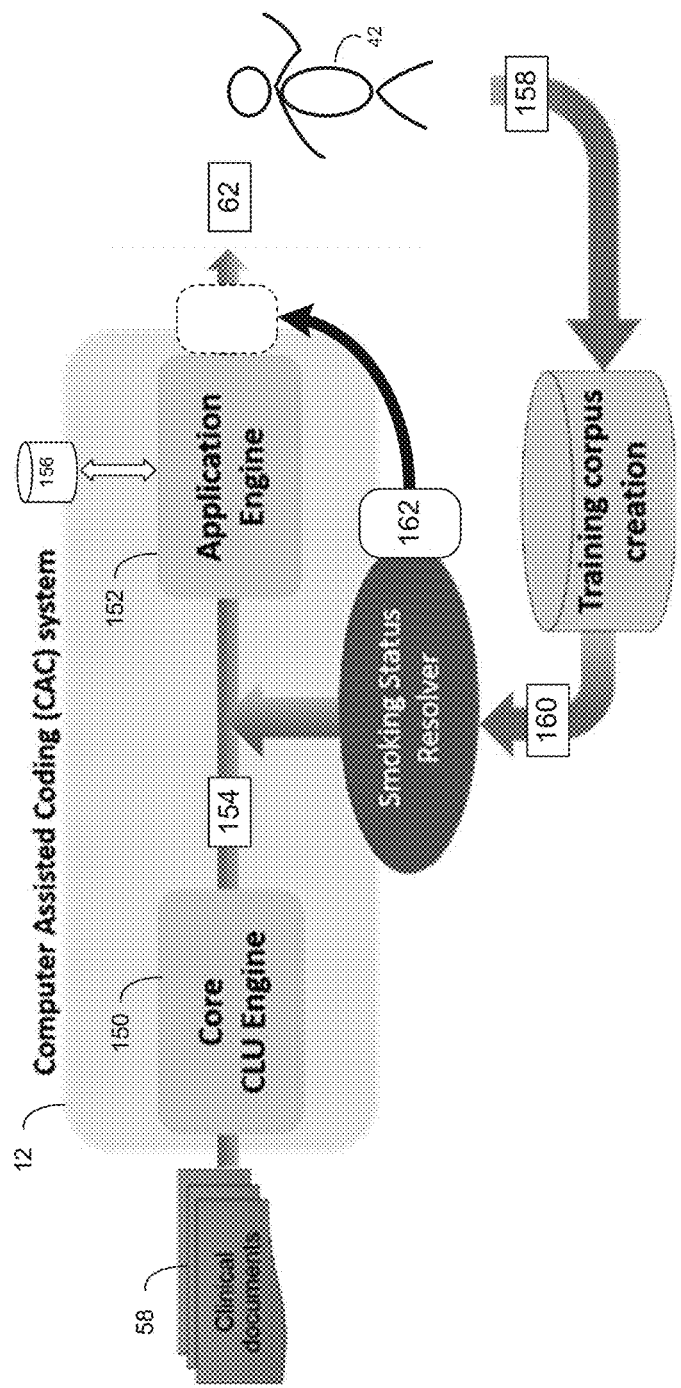
FIG. 3 is a diagrammatic view of the computer assisted coding system of FIG. 1.

Referring also to FIG. 3, computer assisted coding system 12 may be configured to be specific to the healthcare industry and healthcare data. Computer assisted coding system 12 may include Clinical Language Understanding (CLU) engine 150 that may be configured to process content 58 in order to gain an understanding of the patient encounters defined within content 58. For example, CLU engine 150 may be configured to extract clinical facts (included within content 58) that are relevant to current (and historical) conditions of the patients that are the subject of content 58.

Computer assisted coding system 12 may further include application engine 152 that may be configured to be specific to the task of medical coding. For example, application engine 152 may utilizes various rules and/or standards to process content 58 and generate billing codes 62, wherein examples of billing codes 62 may include but are not limited to ICD10 billing codes. As is known in the art, ICD10 billing codes are the 10$^{th}$ revision of the International Statistical Classification of Diseases and Related Health Problems (ICD), a medical classification list by the World Health Organization (WHO) that contains codes for diseases, signs and symptoms, abnormal findings, complaints, social circumstances, and external causes of injury or diseases.

The CLU Engine:

CLU engine 150 may be configured to extract and normalize clinically relevant information from text, using Natural Language Processing technology, wherein this extraction phase (which may involve the detection and classification of useful pieces of information within content 58) may include multiple operations/processes. For example, the extraction phrase effectuated by CLU engine 150 may include one or more of:

The tokenization of content 58, wherein content 58 may be segmented into minimal individual text units (e.g., words, groups of words, phrases, sentences, punctuation marks, etc.).

The classification of content 58 into different relevant clinical types (e.g., "Progress Note", "History and Physical", "Consultation", "Procedure Note", "Client Intake", "Client Check-Out", etc.).

The detection of regions within content 58 that form clinically relevant sections (e.g., "Past Medical History section", "Medications section", "Laboratory Results section", "Chief Complaint section", "Assessment & Plan section", etc.).

The detection of disorders, findings, medications, allergies, substance use, vital signs, and procedures entities within content 58, as well as the detection of relations/ relationships between these entities (and possible attributes such as negation, hedge, laterality, body sites, qualifiers, status, frequency, form, dosage, etc.).

The generation and normalization of medical facts, wherein an entity plus all of its attributes may form a medical fact and these medical facts may be normalized by CLU engine 150 to their canonical form using a standardized terminology of medical terms.

These normalized medical facts (e.g., medical facts 154) may be provided by CLU engine 150 (together with other relevant information, such as e.g., section information and document types) to application engine 152 so that billing codes 62 may be assigned.

The Application Engine

Application engine 152 may be configured to process the entire patient encounter (by processing medical facts 154) and produce a set of billing codes (e.g., billing codes 62) appropriate for the patient encounter(s) defined within content 58, wherein application engine 152 may be configured to process the above-described normalized medical facts (e.g., medical facts 154) without access to the raw content (e.g., content 58). For example, if content 58 concerns 1,000 individual patient encounters that concern 1,000 individual patients that occurred during a one month period, medical facts 154 may define the medical facts (generated by CLU engine 150) for the 1,000 individual patient encounters and billing codes 62 may include 1,000 sets of billing codes that correspond to the 1,000 individual patient encounters.

Coding rules (e.g., coding rules 156) may be applied by application engine 152 to determine billing codes 62. For example, medical facts 154 may be mapped to e.g., the ICD10 billing code space via e.g., coding rules 156 and bill coding logic included within application engine 152 may be applied to produce billing codes 62. For instance, application engine 152 may utilize coding rules 156 to determine which billing code to use when e.g., two billing codes are mutually exclusive and a first billing code represents a more specific clinical condition and the second billing code represents a more general clinical condition.

Continuing with the above-stated example, assume that the social habit status defined within content 58 concerns the smoking status (e.g., heavy smoker, light smoker, past smoker, never smoked) of plurality of users 60. Since application engine 152 may utilize coding rules 156 to determine which billing code to use when e.g., there are multiple conflicting billing codes, in the event that a portion of content 58 (that concerns a specific patient encounter for a specific patient) contains information that the specific patient is simultaneously e.g., a) heavy smoker, b) an ex-smoker and c) a non-smoker, medical facts 154 may include conflicting facts concerning whether this specific patient is a) a heavy smoker, b) an ex-smoker and c) a non-smoker. Accordingly, application engine 152 may apply one or more selection rules (included within coding rules 158) to determine which of (in this example) the three conflicting facts to utilize when defining billing codes 62.

Automated training process 10 may provide 102 the one or more billing codes (e.g., billing codes 62) concerning the social habit status (e.g., smoking status) of the one or more patients (e.g., plurality of patients 60) to a user (e.g., user 42) for review. Assume for this example that user 42 is a billing coder that works for the clinical environment and is tasked with reviewing billing codes 62. Accordingly, user 42 may review billing codes 62 and may provide feedback 158 to automated training process 10 concerning the same.

Automated training process 10 may receive 104 feedback 158 from user 42 concerning the accuracy of the one or more billing codes (e.g., billing code 62), wherein automated training process 10 may automatically process 106 feedback 158 concerning the one or more billing codes (e.g., billing codes 62) to define one or more confidence scores (e.g., confidence scores 160).

For example and when automatically processing 106 feedback 158 concerning the one or more billing codes (e.g., billing codes 62) to define one or more confidence scores (e.g., confidence scores 160), automated training process 10 may identify 108 a plurality of portions of the content (e.g., content 58) that concern differing social habit statuses of one or more of plurality of patients 60;

define 110 a billing code accuracy score for each of the plurality of portions of the content (e.g., content 58) that concern differing social habit statuses of one or more of plurality of patients 60; and define 112 the one or more confidence scores (e.g., confidence scores 160) based, at least in part, upon the billing code accuracy score defined for each of the plurality of portions of the content (e.g., content 58) that concern differing social habit statuses of one or more of plurality of patients 60.

Further and as will be discussed below in greater detail, automated training process 10 may train 114 computer assisted coding system 12 based, at least in part, upon the one or more confidence scores (e.g., confidence scores 160), wherein training 114 computer assisted coding system 102 based, at least in part, upon the one or more confidence scores (e.g., confidence scores 160) may include: defining 116 a model (e.g., model 162) based, at least in part, upon the one or more confidence scores (e.g., confidences scores 160) and applying 118 the model (e.g., model 162) to an output of computer assisted coding system 102.

In traditional systems, feedback 158 concerning billing codes 62 is manually reviewed (e.g., by an administrator of computer assisted coding system 12) and CLU engine 150 and/or application engine 152 (of computer assisted coding system 12) may be manually tuned/revised in response to feedback 158. However and as discussed above, automated training process 10 may automatically process 106 feedback 158 concerning billing codes 62) to define one or more confidence scores (e.g., confidence scores 160). Accordingly, automated training process 10 does not require human intervention to process feedback 158, since automated training process 10 automatically consumes feedback 158 and tunes computer assisted coding system 12 accordingly.

Containing with the above-stated example, when user 42 reviews billing codes 62, user 42 may accept, reject or modify one or more of billing codes 62, wherein the accepting/rejecting/modifying of billing codes 62 may form the basis of feedback 158. Automated training process 10 may then automatically process 106 feedback 158 concerning billing codes 62 to define confidence scores 160.

As discussed above, automated training process 10 may identify 108 a plurality of portions of the content (e.g., content 58) that concern differing social habit statuses (e.g., when a patient is simultaneously defined as a) a heavy smoker, b) an ex-smoker and c) a non-smoker) of one or more of plurality of patients 60. Specifically, automated training process 10 may examine content 58 and may extract the portions (e.g., sentences and/or regions containing smoking evidences) of content 58 that simultaneously define a specific patient as a a) a heavy smoker, b) an ex-smoker and c) a non-smoker.

Suppose for this example that automated training process 10 identified 108 three portions of content 58 that concern the smoking habits of the patient. Specifically, assume that content 58 being processed by automated training process 10 includes three different fields that address smoking, namely: a) data field A, which is a data field that is used during client intake wherein a receptionist asks the patient if they smoke, b) data field B, which is a data field that is populated by the doctor when the doctor asks the patient if they smoke, and c) data field C, which is a free form field that may be populated by the doctor/physician's assistant during a patient encounter.

Further and as discussed above, automated training process 10 may define 110 a billing code accuracy score for each of the plurality of portions of the content (e.g., content 58) that concern differing social habit statuses (e.g., when a patient is simultaneously defined as a) a heavy smoker, b) an ex-smoker and c) a non-smoker) of one or more of plurality of patients 60). Specifically, automated training process 10 may automatically attach labels to these portions of the content (e.g., content 58) that concern differing social habit statuses that indicate e.g., their correctness and/or alignment with the feedback 158 or their incorrectness and/or misalignment with feedback 158. The labels automatically attached to portions of content 58 by automated training process 10 may include both positive labels and negative labels.

Positive labels (e.g., a binary 1) may be represented by (in this example) smoking evidences (i.e. normalized medical facts representing smoking habits) extracted by CLU engine 150 that align with (e.g., are the same as) the billing codes defined within feedback 158. For example, assume that CLU engine 150 detected and normalized the medical fact of "ex-smoker" and the billing code provided by user 42 in feedback 158 was also for an ex-smoker, as shown below:

Clinical document states: "Patient is a former smoker."
CLU medical fact "former smoker", which is normalized to "8517006: EX-SMOKER"
Customer feedback: "Z87.891: Personal history of nicotine dependence"

Conversely, negative labels (e.g., a binary 0) may be represented by (in this example) smoking evidences (i.e. normalized medical facts representing smoking habits) extracted by CLU engine 150 that conflict with (e.g., are different from) the billing codes defined within feedback 158. For example, assume that CLU engine 150 detected and normalized the medical fact for "smoker", but the billing code provided by user 42 in feedback 158 was for an ex-smoker, as shown below:

Clinical document states: "Patient quit smoking long time ago."
CLU medical fact "smoking", which is normalized to "77176002: SMOKER"
Customer feedback: "Z87.891: Personal history of nicotine dependence"

Continuing with the above-stated example and as discussed above, content 58 includes (in this example) three different fields that address smoking, namely: a) data field A, b) data field B, and c) data field C, wherein automated training process 10 may define 110 a billing code accuracy score for each of these three data fields. For example, automated training process 10 may define 110 a binary 1 to any of data fields A, B, C whenever feedback 158 indicates that the billing code (defined within billing codes 62) that was associated with the normalized medical fact (defined within medical facts 154) that was related to the data field in question was accurate/correct; while automated training process 10 may define 110 a binary 0 to any of data fields A, B, C whenever feedback 158 indicates that the billing code (defined within billing codes 62) that was associated with the normalized medical fact (defined within medical facts 154) that was related to the data field in question was inaccurate/incorrect, As discussed above, automated training process 10 may define 112 the one or more confidence scores (e.g., confidence scores 160) based, at least in part, upon the billing code accuracy score defined 110 for each of the plurality of portions of the content (e.g., content 58) that concern differing social habit statuses of one or more of plurality of patients 60.

Accordingly, automated training process 10 may examine the above-described binary 1s and binary 0s define 110 for each of (in this example) data field A, data field B, and/or data field C to determine the average accuracy of those fields. For example, assume that being data field A is populated by a receptionist, patients are more likely to lie to a receptionist and, it is determined, that data field A is typically only 32% accurate (as binary is only represent 32% of all of the grades assigned to data field A). Further, assume that being data field B is populated by a doctor, patients are much less likely to lie to a doctor and, it is determined, that data field B is typically 91% accurate (as binary 1s represent 91% of all of the grades assigned to data field B). Additionally, assume that being data field C is a free form data field and (being it lacks structure) it is determined that data field C is typically only 53% accurate (as binary 1s represent 53% of all of the grades assigned to data field C). Accordingly, automated training process 10 may define 112 a confidence score of 32% for data field A, a confidence score of 91% for data field B, and a confidence score of 53% for data field C.

Classifier Features

Automated training process 10 may use the above-described extracted portions and various classification features included within the above-described extracted portions to automatically train a multi-layer Neural Network classifier that defines 112 the above-described confidence scores (e.g., confidence score 160) for each patient's smoking status among all the conflicting statuses reported during the patient encounter. Such a confidence score (e.g., confidence score 160) may represent the likelihood of a particular incidence of the smoking status being correct.

Accordingly and as discussed above, automated training process 10 defined 112 (in this example) a confidence score of 32% for data field A, a confidence score of 91% for data field B, and a confidence score of 53% for data field C. So, in the event that data field A defined a patient as a "nonsmoker" (which has a confidence score of 32%), data field B defined the same patient as being a "heavy smoker" (which has a confidence score of 91%), and data field C defined the same patient as being an "ex-smoker" (which has a confidence score of 53%), automated training process 10 may default to defining the patient as a "heavy smoker" and assigning a "heavy smoker" billing code to the patient encounter of this patient for billing purposes.

The above-stated classifier features may be pieces of information extracted from content 58 and/or from the normalized medical facts (e.g., medical facts 154) that may help automated training process 10 determine the correct confidence score for (in this example) the smoking status of the patient(s).

Examples of classifier features may include but are not limited to:
- lexical features corresponding to the surrounding words of the smoking evidence or medical fact;
- structural features from the sentence where the smoking evidence was detected (e.g., the number of words, characters, special characters and digits);
- regular expression features that capture negation, speculation, history and family history related terms from the same sentence where the smoking evidence was found;
- dictionary lookup features for disorders, findings, medications, and procedures found in the same clinical document as the smoking evidence;
- disorders, findings and procedures together with their attributes that were found in the same clinical document as the smoking evidence;
- medical sections where the smoking evidence was found; and/or
- other smoking medical facts present in the same document.

Operational Examples

Accordingly, assume that automated training process 10 is presented with the following clinical document:

The patient is admitted for increased shortness of breath [ . . . ] She reports to me that she quit smoking four months ago but apparently told the admitting physician that she still smokes daily. Her husband reported to the admitting physician that she smokes 10-20 cigarettes per day.

Automated training process 10 may identify 108 three portions of the above-described clinical document (e.g., a portion of content 58) that concern differing smoking statuses for this patient; may define 110 a billing code accuracy score for each of these three portions of content 58; and may define 112 a confidence score for each of these three smoking statuses, and may rank them as follows:

| Ranking | Evidence | Score |
| --- | --- | --- |
| 1 | "smokes 10-20 cigarettes per day" | 0.8 |
| 2 | "smokes daily" | 0.7 |
| 3 | "quit smoking" | 0.3 |

Based on above-described rankings, the smoking status (and billing code) for the patient associated with the above-described clinical document may be that of a cigarette smoker, i.e. "F17.210—Nicotine dependence, cigarettes, uncomplicated".

Further, assume that automated training process 10 is presented with the following clinical document:

| Social History Main Topics |
| --- |
| Smoking Status: Current Every Day Smoker Packs/Day: 1.00 Years: 70 Types: Cigarettes Comment: Must stop smoking |

Automated training process 10 may identify 108 two portions of the above-described clinical document (e.g., a portion of content 58) that concern differing smoking statuses for this patient; may define 110 a billing code accuracy score for each of these two portions of content 58; and may define 112 a confidence score for each of these two smoking statuses, and may rank them as follow:

| Ranking | Evidence | Score |
| --- | --- | --- |
| 1 | "Current Every Day Smoker Packs/Day: 1.00 Years: 70 Types: Cigarettes" | 0.9 |
| 2 | "stop smoking" | 0.2 |

Based on above-described rankings, the smoking status (and billing code) for the patient associated with the above-described clinical document may be that of a cigarette smoker, i.e., "F17.210—Nicotine dependence, cigarettes, uncomplicated".

As discussed above, automated training process 10 may train 114 computer assisted coding system 12 based, at least in part, upon the one or more confidence scores (e.g., confidence scores 160), wherein training 114 computer assisted coding system 102 based, at least in part, upon the one or more confidence scores (e.g., confidence scores 160) may include: defining 116 a model (e.g., model 162) based, at least in part, upon the one or more confidence scores (e.g., confidences scores 160) and applying 118 the model (e.g., model 162) to an output of computer assisted coding system 102.

Accordingly and when wherein training 114 computer assisted coding system 102, automated training process 10 may define 116 a model (e.g., model 162) based, at least in part, upon the above-described confidence scores (e.g., confidences scores 160) and may apply 118 the model (e.g., model 162) to an output of computer assisted coding system 102. Therefore and with respect to data field A, data field B and data field C, automated training process 10 may define 116 model 162 to greatly favor the status defined within data field B (as it has a 91% confidence score), wherein model 162 may be applied 118 to the output of computer assisted coding system 102 so that, in this example, it proactively influences billing codes 62 to favor data field B in the event of ambiguity with respect to smoking status defined within data field B.

General:

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method, executed on a computing device, comprising:
   processing content concerning a plurality of patients using a computer assisted coding (CAC) system to define one or more billing codes concerning a social habit status of one or more patients of the plurality of patients;
   receiving, from a human user, feedback concerning accuracy of the one or more billing codes, wherein receiving the feedback comprises receiving user input indicating whether the one or more billing codes were accepted, rejected or modified by the human user;
   automatically processing the feedback concerning the accuracy of the one or more billing codes to define one or more confidence scores, wherein automatically processing the feedback comprises automatically processing the received user input indicating whether the one or more billing codes were accepted, rejected or modified by the human user to define the one or more confidence scores;
   defining a first confidence score based on a first billing code accuracy score for a first portion of the content that concerns a first social habit status of a patient;
   defining a second confidence score based on a second billing code accuracy score for a second portion of the content that concerns a second social habit status of the patient, wherein the second confidence score is higher than the first confidence score; and
   training the CAC system based, at least in part, upon the one or more confidence scores, wherein training the CAC system based, at least in part, upon the one or more confidence scores comprises training, based on the first and second confidence scores, a model that in determining a social habit status for a subsequent content favors a social habit status associated with a second portion of the subsequent content over a social habit status associated with a first portion of the subsequent content.

2. The computer-implemented method of claim 1, wherein the social habit status of one or more patients includes one or more of:
   a smoking status of the one or more patients;
   a drinking status of the one or more patients; and
   a drug use status of the one or more patients.

3. The computer-implemented method of claim 1, wherein automatically processing the feedback concerning the accuracy of the one or more billing codes to define the one or more confidence scores includes:
   identifying a plurality of portions of the content that concern differing social habit statuses of the patient.

4. The computer-implemented method of claim 3, wherein automatically processing the feedback concerning the accuracy of the one or more billing codes to define the one or more confidence scores further includes:
   defining a billing code accuracy score for each of the plurality of portions of the content that concern differing social habit statuses of the patient.

5. The computer-implemented method of claim 4, wherein automatically processing the feedback concerning the accuracy of the one or more billing codes to define the one or more confidence scores further includes:
   defining the one or more confidence scores based, at least in part, upon the billing code accuracy score defined for each of the plurality of portions of the content that concern differing social habit statuses of the patient.

6. The computer-implemented method of claim 1, wherein training the CAC system based, at least in part, upon the one or more confidence scores includes:
   applying the model to an output of the CAC system.

7. A computer program product residing on a non-transitory computer readable medium having a plurality of instructions stored thereon which, when executed by a processor, cause the processor to perform operations comprising:
   processing content concerning a plurality of patients using a computer assisted coding (CAC) system to define one or more billing codes concerning a social habit status of one or more patients of the plurality of patients;
   receiving, from a human user, feedback concerning accuracy of the one or more billing codes, wherein receiving the feedback comprises receiving user input indicating whether the one or more billing codes were accepted, rejected or modified by the human user;
   automatically processing the feedback concerning the accuracy of the one or more billing codes to define one or more confidence scores, wherein automatically processing the feedback comprises automatically processing the received user input indicating whether the one or more billing codes were accepted, rejected or modified by the human user to define the one or more confidence scores;
   defining a first confidence score based on a first billing code accuracy score for a first portion of the content that concerns a first social habit status of a patient;
   defining a second confidence score based on a second billing code accuracy score for a second portion of the content that concerns a second social habit status of the patient, wherein the second confidence score is higher than the first confidence score; and training the CAC system based, at least in part, upon the one or more confidence scores, wherein training the CAC system based, at least in part, upon the one or more confidence scores comprises training, based on the first and second confidence scores, a model that in determining a social habit status for a subsequent content favors a social habit status associated with a second portion of the subsequent content over a social habit status associated with a first portion of the subsequent content.

8. The computer program product of claim 7, wherein the social habit status of one or more patients includes one or more of:
a smoking status of the one or more patients;
a drinking status of the one or more patients; and
a drug use status of the one or more patients.

9. The computer program product of claim 7, wherein automatically processing the feedback concerning the accuracy of the one or more billing codes to define the one or more confidence scores includes:
identifying a plurality of portions of the content that concern differing social habit statuses of the patient.

10. The computer program product of claim 9, wherein automatically processing the feedback concerning the accuracy of the one or more billing codes to define the one or more confidence scores further includes:
defining a billing code accuracy score for each of the plurality of portions of the content that concern differing social habit statuses of the patient.

11. The computer program product of claim 10, wherein automatically processing the feedback concerning the accuracy of the one or more billing codes to define the one or more confidence scores further includes:
defining the one or more confidence scores based, at least in part, upon the billing code accuracy score defined for each of the plurality of portions of the content that concern differing social habit statuses of the patient.

12. The computer program product of claim 7, wherein training the CAC system based, at least in part, upon the one or more confidence scores includes:
applying the model to an output of the CAC system.

13. A computing system including a processor and memory configured to perform operations comprising:
processing content concerning a plurality of patients using a computer assisted coding (CAC) system to define one or more billing codes concerning a social habit status of one or more patients of the plurality of patients;
receiving, from a human user, feedback concerning accuracy of the one or more billing codes, wherein receiving the feedback comprises receiving user input indicating whether the one or more billing codes were accepted, rejected or modified by the human user;
automatically processing the feedback concerning the accuracy of the one or more billing codes to define one or more confidence scores, wherein automatically processing the feedback comprises automatically processing the received user input indicating whether the one or more billing codes were accepted, rejected or modified by the human user to define the one or more confidence scores;

defining a first confidence score based on a first billing code accuracy score for a first portion of the content that concerns a first social habit status of a patient;

defining a second confidence score based on a second billing code accuracy score for a second portion of the content that concerns a second social habit status of the patient, wherein the second confidence score is higher than the first confidence score; and training the CAC system based, at least in part, upon the one or more confidence scores, wherein training the CAC system based, at least in part, upon the one or more confidence scores comprises training, based on the first and second confidence scores, a model that in determining a social habit status for a subsequent content favors a social habit status associated with a second portion of the subsequent content over a social habit status associated with a first portion of the subsequent content.

14. The computing system of claim 13, wherein the social habit status of one or more patients includes one or more of:
a smoking status of the one or more patients;
a drinking status of the one or more patients; and
a drug use status of the one or more patients.

15. The computing system of claim 13, wherein automatically processing the feedback concerning the accuracy of the one or more billing codes to define the one or more confidence scores includes:
identifying a plurality of portions of the content that concern differing social habit statuses of the patient.

16. The computing system of claim 15, wherein automatically processing the feedback concerning the accuracy of the one or more billing codes to define the one or more confidence scores further includes:
defining a billing code accuracy score for each of the plurality of portions of the content that concern differing social habit statuses of the patient.

17. The computing system of claim 16, wherein automatically processing the feedback concerning the accuracy of the one or more billing codes to define the one or more confidence scores further includes:
defining the one or more confidence scores based, at least in part, upon the billing code accuracy score defined for each of the plurality of portions of the content that concern differing social habit statuses of the patient.

18. The computing system of claim 13, wherein training the CAC system based, at least in part, upon the one or more confidence scores includes:
applying the model to an output the CAC system.

19. The computer-implemented method of claim 3, wherein identifying the plurality of portions of the content that concern differing social habit statuses of the patient comprises:
identifying the plurality of portions of the content that simultaneously specify conflicting social habit statuses of the patient.

20. The computer-implemented method of claim 4, wherein defining the billing code accuracy score for each of the plurality of portions of the content that concern differing social habit statuses of the patient comprises:
determining, for each of the plurality of portions of the content, whether a respective social habit status indicated in the portion of the content aligns with the feedback.

* * * * *